(12) United States Patent
Wang et al.

(10) Patent No.: US 10,598,585 B2
(45) Date of Patent: Mar. 24, 2020

(54) SYNCHRONOUS HIGH-SPEED PHOTOGRAPHING METHOD AND DEVICE FOR MICROPARTICLE ROTATION IN LIQUID CYCLONE FIELD

(71) Applicant: EAST CHINA UNIVERSITY OF SCIENCE AND TECHNOLOGY, Shanghai (CN)

(72) Inventors: Hualin Wang, Shanghai (CN); Yuan Huang, Shanghai (CN); Yang Qiu, Shanghai (CN); Pengbo Fu, Shanghai (CN); Yanhong Zhang, Shanghai (CN); Zhishan Bai, Shanghai (CN); Qiang Yang, Shanghai (CN); Fengqin He, Shanghai (CN)

(73) Assignee: EAST CHINA UNIVERSITY OF SCIENCE AND TECHNOLOGY, Shanghai (CN)

( * ) Notice: Subject to any disclaimer, the term of this patent is extended or adjusted under 35 U.S.C. 154(b) by 396 days.

(21) Appl. No.: 15/324,552

(22) PCT Filed: Jun. 15, 2015

(86) PCT No.: PCT/CN2015/081425
§ 371 (c)(1),
(2) Date: Jan. 6, 2017

(87) PCT Pub. No.: WO2016/004810
PCT Pub. Date: Jan. 14, 2016

(65) Prior Publication Data
US 2018/0356329 A1    Dec. 13, 2018

(30) Foreign Application Priority Data

Jul. 8, 2014   (CN) .......................... 2014 1 0323142
Jul. 8, 2014   (CN) .......................... 2014 1 0323160

(51) Int. Cl.
G01N 15/14    (2006.01)
H04N 5/247    (2006.01)
(Continued)

(52) U.S. Cl.
CPC ......... *G01N 15/14* (2013.01); *G01N 15/1429* (2013.01); *G01P 3/38* (2013.01);
(Continued)

(58) Field of Classification Search
CPC ...... G01N 15/14; G01N 15/1429; G01P 3/38; G06T 2207/30241; G06T 7/292; G06T 7/70; H04N 5/247
(Continued)

(56) References Cited

U.S. PATENT DOCUMENTS 5,440,144 A       8/1995  Raffel et al.
5,883,707 A  *    3/1999  Arndt ...................... G01P 5/001
                                                         356/28
(Continued)

FOREIGN PATENT DOCUMENTS

CN    101509931 A    8/2009
CN    102435770 A    5/2012
(Continued)

OTHER PUBLICATIONS

Simon Kleinl, Mathieu Gibert1,4,Antoine Berut1 and Eberhard "Simultaneous 3D measurement of the translation and rotation of finite-size particles and the flow field in a fully developed turbulent water flow" (Year: 2012).*
(Continued)

*Primary Examiner* — Brian T Pendleton
*Assistant Examiner* — Alan H Luong
(74) *Attorney, Agent, or Firm* — Dinsmore & Shohl LLP

(57) ABSTRACT

A method and a device for synchronous high-speed photographing of microparticle rotation in a liquid cyclone field
(Continued)

and for determining the rotation velocity of a microparticle in a liquid cyclone field by using a combination of a synchronous high-speed photographing system and a transparent microparticle containing two centrosymmetrically arranged inner cores having the same diameter. The method comprises: using a transparent microparticle comprising two inner cores having the same diameter and arranged centrosymmetrically as a rotation test particle; acquiring synchronously two groups of two dimensional image series of microparticle motion in a liquid cyclone field using two orthogonally arranged high-speed digital cameras; and reconstructing a three dimensional motion trajectory of the microparticle from the two groups of synchronous image series, and determining a rotation velocity of the microparticle in the cyclone field at the same time.

16 Claims, 3 Drawing Sheets

(51) Int. Cl.
 *G06T 7/292* (2017.01)
 *G01P 3/38* (2006.01)
 *G06T 7/246* (2017.01)
 *G01N 15/10* (2006.01)
 *H04N 5/235* (2006.01)
 *G06T 7/70* (2017.01)

(52) U.S. Cl.
 CPC .............. *G06T 7/246* (2017.01); *G06T 7/292* (2017.01); *H04N 5/247* (2013.01); *G01N 15/1468* (2013.01); *G01N 2015/1075* (2013.01); *G01N 2015/1445* (2013.01); *G06T 7/70* (2017.01); *G06T 2207/10016* (2013.01); *G06T 2207/30241* (2013.01); *H04N 5/2354* (2013.01)

(58) Field of Classification Search
 USPC ........................................................ 348/135
 See application file for complete search history.

(56) References Cited

U.S. PATENT DOCUMENTS

| | | | | |
|---|---|---|---|---|
| 2006/0244964 | A1* | 11/2006 | Cox | G01N 15/1456 356/336 |
| 2009/0025489 | A1* | 1/2009 | Christensen | G01N 21/645 73/864 |
| 2013/0122301 | A1* | 5/2013 | Mastrangelo | G01F 1/704 428/402 |
| 2014/0087412 | A1* | 3/2014 | Fouras | B01L 3/502761 435/29 |

FOREIGN PATENT DOCUMENTS

| | | | |
|---|---|---|---|
| CN | 102435770 | * | 6/2012 |
| CN | 102494869 | * | 6/2012 |
| CN | 102494869 | A | 6/2012 |
| CN | 102853990 | * | 1/2013 |
| CN | 102853990 | A | 1/2013 |
| CN | 102944507 | A | 2/2013 |
| CN | 103197095 | A | 7/2013 |
| CN | 104049100 | A | 9/2014 |
| CN | 104062091 | A | 9/2014 |
| DE | 19928698 | A1 | 9/2000 |
| JP | H08136567 | A | 5/1996 |
| KR | 20090114125 | A | 11/2009 |

OTHER PUBLICATIONS

Liu Yi1 Wang Hualin2 Yang "Experimental investigation on aggregation of ultrafine particles in swirling flow field" (Year: 2010).*
Colin R. Meyer, Margaret L. Byron, and Evan A. Variano. "Rotational diffusion of particles in turbulence" (Year: 2013).*
International Search Report dated Sep. 22, 2015 related to PCT/CN2015/081425 filed Jun. 15, 2015.
Meyer, et al, Rotational Diffusion of Particles in Turbulence, journal, 2013, pp. 89-102, vol. 3, Association for the Sciences of Limnology and Oceanography, Inc., USA.
Klein et al., Simultaneous 3D measurement of the translation and rotation of finite-size particles and the flow field in a fully developed turbulent water flow, journal, 2013, pp. 1-10, vol. 24, Measurement Science and Technology, USA.
Yi, et al, Experimental investigation on aggregation of ultrafine particles in swirling flow field, journal, Mar. 2010, pp. 1-4, vol. 4—No. 3, Chinese Journal of Environmental Engineering, China.

* cited by examiner

SYNCHRONOUS HIGH-SPEED PHOTOGRAPHING METHOD AND DEVICE FOR MICROPARTICLE ROTATION IN LIQUID CYCLONE FIELD

CROSS REFERENCE TO RELATED APPLICATIONS

This present specification claims priority to International Patent Application No. PCT/CN2015/081425 filed on Jun. 15, 2015 entitled "Synchronous High-speed Photographing Method And Device For Microparticle Rotation In Liquid Cyclone Field," which claims priority to CN Application Number 201410323142.1 filed Jul. 8, 2014 and CN Application Number 20141323160.X filed on Jul. 8, 2014, the entirety of which are incorporated by reference herein.

TECHNICAL FIELD

The disclosure pertains to the field of determining liquid-solid two-phase flow, and relates to a method and a device for determining microparticle rotation motion in a liquid cyclone field using a high-speed photographing system. More particularly, there are provided a method and a device for determining synchronously microparticle rotation motion in a liquid cyclone field using two orthogonally arranged high-speed digital cameras.

BACKGROUND

Owing to the advantages of high efficiency, reduced energy consumption, etc., the liquid-solid cyclone separation technology is widely used in oil refining and chemical production. Along with the development of the heavy oil refining technology, recovery and treatment of waste porous catalysts containing oil becomes a challenge restricting the development of oil refining technologies. The cyclone-scrubbing-desorption technology solves effectively the problem of deoiling porous particles containing oil. It has been found in the research on the cyclone-scrubbing-desorption technology that microparticles not only revolve around the cyclone field center (liquid-solid cyclone separation in traditional sense), but also rotate around instantaneous axes of their own. The rotation motion of the particles reinforces separation of oil entrapped in the particles. In order to study the effect of microparticle rotation motion in reinforcing separation of pollutants in a cyclone field, there is proposed a method of determining microparticle rotation motion in a cyclone field, and there is developed a test device.

Many efforts have been devoted to the study of rotation motion of particles suspended in a liquid shear flow field. However, due to the complexity of the flow field and the restriction of the test techniques, the study is basically limited to simple shear flow under a condition of small particle Reynolds numbers. Little study has been done on particle rotation motion in turbulence with high particle Reynolds numbers.

Simon Klein, et al. (Measurement Science and Technology, 2013, Vol. 24, No. 2, pp. 1-10) reported a test technique that measures simultaneously in three dimensions the trajectories, the translation, and the rotation of finite-size inertial particles together with the turbulence flow, wherein three high-speed CMOS cameras were used to measure the three dimensional trajectories of the particles by an LPT method, and the rotation motion of the particles in a von Kármán flow field was analyzed by tracking the temporal evolution of a plurality of 100 μm fluorescent particles embedded in the surface of the spherical particles of a super water absorbent polymer. Due to the super water absorbing capacity, the polymer particles grew from 1-2 mm to about 10 mm in diameter after immersed in water, and the density of the particles was comparable with water. The frame frequency of the three high-speed CMOS cameras was 2900 fps, and the image resolution was 768×768.

Colin R. Meyer, et al (Rotational diffusion of particles in turbulence, arXiv preprint arXiv:1301.0150, 2013) determined the rotation motion of spherical and elliptical particles in a symmetrically stirred tank using stereoscopic particle image velocimetry (SPIV). The diameter of the spherical particles was 8 mm, and the major and minor axes of the elliptical particles were 16 mm and 8 mm. The density of the particles was 1007 kg/m$^3$. The particle Reynolds numbers of the spherical and elliptical particles in the flow field were 22 and 63, respectively. The time resolution (frame frequency of the camera) in the measurement was 14.773 Hz. The measured rotation velocity was $[\Omega_x,\Omega_y,\Omega_z]=[-0.012,-0.029,0.021]$ Rad/s for the spherical particles, and $[\Omega_x,\Omega_y,\Omega_z]=[-0.024,-0.052,0.011]$ Rad/s for the elliptical particles.

However, for a liquid-solid micro-cyclone, the maximum tangent velocity in the cyclone field was up to 8-10 m/s, and the diameter of the particles to be separated was generally on the micron scale. This may require higher time and space resolution in measurement.

In view of the above problems, starting from increasing the identifiability of rotating particles, a need exists for methods and a devices for determining synchronously the revolution and rotation of a microparticle in a cyclone field using stereoscopic high-speed digital photographing technique.

SUMMARY

The disclosure provides a synchronous high-speed photographing method for measuring the rotation speed of a microparticle in a liquid cyclone field and a device for the same purpose, thereby providing a reliable means for measuring the rotation speed of a microparticle in a fluid characterized by low viscosity and high turbulence.

In one aspect, a synchronous high-speed photographing method for determining the rotation of a microparticle in a liquid cyclone field includes (1) using a transparent microparticle comprising two inner cores having the same diameter and arranged centrosymmetrically as a rotation test particle, (2) acquiring synchronously two groups of two dimensional image series of microparticle motion in a liquid cyclone field using two orthogonally arranged high-speed cameras, and (3) reconstructing a three dimensional motion trajectory of the microparticle from the two groups of synchronous image series, and determining a rotation velocity of the microparticle at the same time by analyzing the overlapping and separating frequency of the projections of the two inner cores in the microparticle in the image series.

In some embodiments, the rotation test particle is a spherical particle having a transparent or translucent shell and containing two centrosymmetrically arranged inner core particles which have a deep color and the same diameter, wherein the test particle has a diameter of less than 500 microns and high monodispersity.

In another embodiment, the two high-speed digital cameras are arranged orthogonally, and the synchronous photographing error is less than 10 microseconds, wherein the depth of field of the two high-speed cameras is no less than 20% of the diameter of the cyclone field.

In another embodiment, the method reconstructs the three dimensional motion trajectory in a zone to be tested by fitting the two dimensional motion trajectories of the microparticle in the two groups of synchronous image series.

In another embodiment, the method determines the rotation velocity of the microparticle by analyzing the overlapping and separating frequency of the projections of the two inner cores in the microparticle in the image series, wherein the test particle has a discrimination precision of rotational angle of 90 degrees.

In another embodiment, the method uses one high-speed camera to determine the rotation velocity of the particle.

In another embodiment, the liquid cyclone field has a maximum tangent velocity of no more than 10 m/s.

In another aspect, a device for synchronous high-speed photographing of microparticle rotation in a liquid cyclone field includes a cyclone separation experimental apparatus for providing a stable cyclone field to be tested; two high-speed digital cameras (HSDC) for synchronous measurement; a large power LED cold light source for providing strong white light; a synchronous trigger for the high-speed digital cameras; and a computer for controlling the high-speed digital cameras and storing data.

In an embodiment, the cyclone separation experimental apparatus is a circulating system, wherein the experimental apparatus comprises a reservoir for storing liquid and a vortex pump connected to the reservoir for pressurizing the liquid, wherein the outlet of the vortex pump divides into two routes, along one of which a fluid goes back to the reservoir through a backflow valve, along the other of which another liquid goes through a flow valve and a particle feeding connector and then enters a quartz glass microcyclone for testing, wherein the fluid from both the top and the bottom of the quartz glass microcyclone returns to the reservoir. A pressure meter is arranged at each of the inlet and two outlets of the quartz glass microcyclone, and a flow meter and a control valve are arranged at the inlet and the top outlet.

In another embodiment, the particle feeder is arranged in front of the inlet of the quartz glass microcyclone, wherein feeding and releasing of a test particle are controlled by two on-off valves.

In another embodiment, one of the high-speed digital cameras has a frame frequency of 10000 fps or more, a minimum exposure time of 1 microsecond or less, and a resolution of 800×600 or more; and the other of the high-speed digital cameras has a frame frequency of 2000 fps or more, a minimum exposure time of 1 microsecond or less, and a resolution of 800×600 or more.

In another embodiment, the two high-speed digital cameras use macrolens.

In another embodiment, the two high-speed digital cameras use a synchronous trigger for external triggering.

In another embodiment, the large power LED cold light source has a lighting color temperature of 5500-8000 K and a luminous flux of 12000 Lm or more.

DETAILED DESCRIPTION

Figure 1:
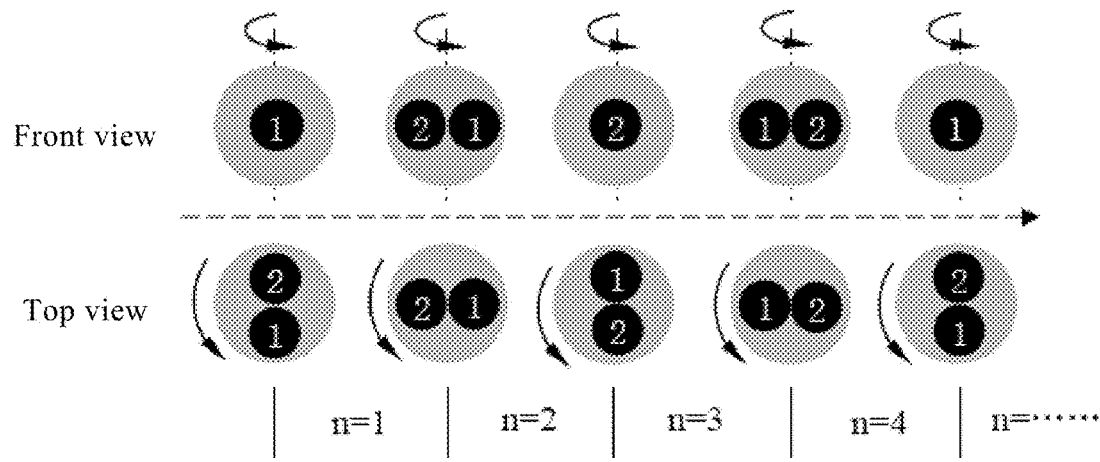
FIG. 1 is a schematic view showing a method of determining the rotation motion of a transparent or translucent microparticle containing two inner cores having the same diameter and arranged centrosymmetrically according to one or more embodiments shown and described herein.

It has been found in the research that particles suspended in a multi-phase flow field exhibit not only motion of spatial displacement along with the continuous phase media, but also motion of rotation around their own instantaneous rotational axes. The rotation motion affects both the macroscopic motion trajectories of the particles and the surrounding flow field. It has been found that particles in a liquid-solid microcyclone also rotate around their own instantaneous axes in addition to macroscopic revolution motion around the center of the cyclone field. However, due to the particular complexity of the flow field in a cyclone and the high-speed motion of particles, it may be difficult to discern the rotation of common particles. Thus, difficulty may exist in determining the rotation motion of microparticles in a cyclone field. In view of the above problems, thus a need exists for increasing the identifiability of particle rotation with the use of synchronous high-speed photographing techniques.

In a first aspect, there is provided a synchronous high-speed photographing method for determining the rotation of a microparticle in a liquid cyclone field, which includes (1) using a transparent or translucent microparticle comprising two inner cores having the same diameter and arranged centrosymmetrically as a rotation test particle, (2) acquiring synchronously two groups of two dimensional image series of microparticle motion in a liquid cyclone field using two orthogonally arranged high-speed digital cameras, and (3) reconstructing a three dimensional motion trajectory of the microparticle from the two dimensional motion of the microparticle in the two groups of synchronous image series, and determining a rotation velocity of the microparticle in the cyclone field at the same time.

The rotation test particle may be a spherical particle having a transparent or translucent shell, wherein the test particle has a diameter of less than 500 microns and high monodispersity, i.e. its coefficient of variation (CV value) being less than 5%. The two inner core particles should have a deep color and the same diameter, and should be centrosymmetrically arranged and opaque.

The method determines the rotation velocity of the microparticle by analyzing the overlapping and separating frequency of the projections of the two inner cores in the microparticle in the two dimensional image series. The test particle has a discrimination precision of rotational angle of 90 degrees. Generally, an image series in which the inner cores overlap two times is used to calculate the rotation velocity of the microparticle.

The two high-speed digital cameras are orthogonally arranged, the synchronous photographing error is not more than 5 microseconds, and the depth of field is not less than 20% of the diameter of the cyclone field.

The liquid cyclone field has a maximum tangent velocity of no more than 10 m/s.

In a second aspect, there is provided a synchronous high-speed photographing device for determining the rotation of a microparticle in a liquid cyclone field, which includes a cyclone separation experimental apparatus 1 for providing a cyclone field to be tested, two high-speed digital cameras 2 for synchronous measurement, a large power LED cold light source 3 for providing strong white light; a synchronous trigger 4 for the high-speed digital cameras; and, a computer 5 for measurement control and data storage.

The cyclone separation experimental apparatus is a circulating system, wherein the experimental apparatus comprises a reservoir 1-1 for storing liquid and a vortex pump 1-2 connected to the reservoir for pressurizing the liquid, wherein the outlet of the vortex pump divides into two routes, along one of which a fluid goes back to the reservoir 1-1 through a backflow valve 1-3-2, along the other of which another liquid goes through a flow valve 1-3-1 and a particle feeding connector 1-4-3 and then enters an optical quartz glass microcyclone 1-5, wherein the fluid from both the top and the bottom of the quartz glass microcyclone 1-5 returns to the reservoir 1-1. A pressure meter is arranged at each of the inlet and two outlets of the quartz glass microcyclone 1-5, and a flow meter 1-3-3 and a control valve 1-3-4 are further arranged at the inlet and the top outlet.

The test steps are as follows:
(1) starting the vortex pump 1-2 of the cyclone separation experimental apparatus, and regulating the flow valve 1-3-1 and the backflow valve 1-3-2 to allow the optical quartz glass microcyclone 1-5 to achieve the working conditions for the test;
(2) starting the large power LED cold light source 3 to irradiate the zone to be tested in the cyclone field with strong light;
(3) loading a test particle into the particle feeder 1-4, and releasing the particles into the inlet of the microcyclone 1-5;
(4) triggering the synchronous trigger 4 to allow the two high-speed digital cameras to photograph the microparticle motion synchronously; and
(5) transmitting the image data from the high-speed digital cameras to the computer 5 and storing them therein.

The two high-speed digital cameras are arranged orthogonally, wherein the high-speed digital camera 2-1 has a frame frequency of 10000 fps or more, a minimum exposure time of 1 microsecond or less, and a resolution of 800×600 or more; and the high-speed digital cameras 2-2 has a frame frequency of 2000 fps or more, a minimum exposure time of 1 microsecond or less, and a resolution of 800×600 or more.

The large power LED cold light source has a lighting color temperature of 5500-8000K and a luminous flux of 12000 Lm or more, so as to form clear images of the particle.

The inlet pressure of microcyclone is 0.1 MPa-0.3 MPa, and the liquid temperature is no more than 50° C.

The quartz glass microcyclone has a nominal diameter of 40 mm or less, and has a purified surface.

The cyclone separation experimental apparatus uses a vortex pump exhibiting small output variation. The flow valve 1-3-1 and the backflow valve 1-3-2 are used to achieve synergic control to improve the precision of regulating the flow into the microcyclone 1-5 and reduce the flow variation, thereby stabilizing the cyclone field in the optical quartz glass microcyclone.

A stainless steel needle having an inner diameter of 1.5 mm is disposed inside the particle feeding connector, wherein the needle injects the test microparticle through the inlet of the microcyclone 1-5 into the cyclone field.

See the accompanying drawings.

FIG. 1 is a schematic view showing a method of determining the rotation motion of a transparent or translucent microparticle containing two inner cores having the same diameter and arranged centrosymmetrically according to at least one embodiment. The rotation of the particle is determined by the overlapping and separation of the projections of the two inner cores in the microparticle. The discrimination precision of the rotational angle of the particle is 90 degrees. n represents the number of times the two inner cores overlap and separate in the image series of the rotation motion of the microparticle.

Figure 2:
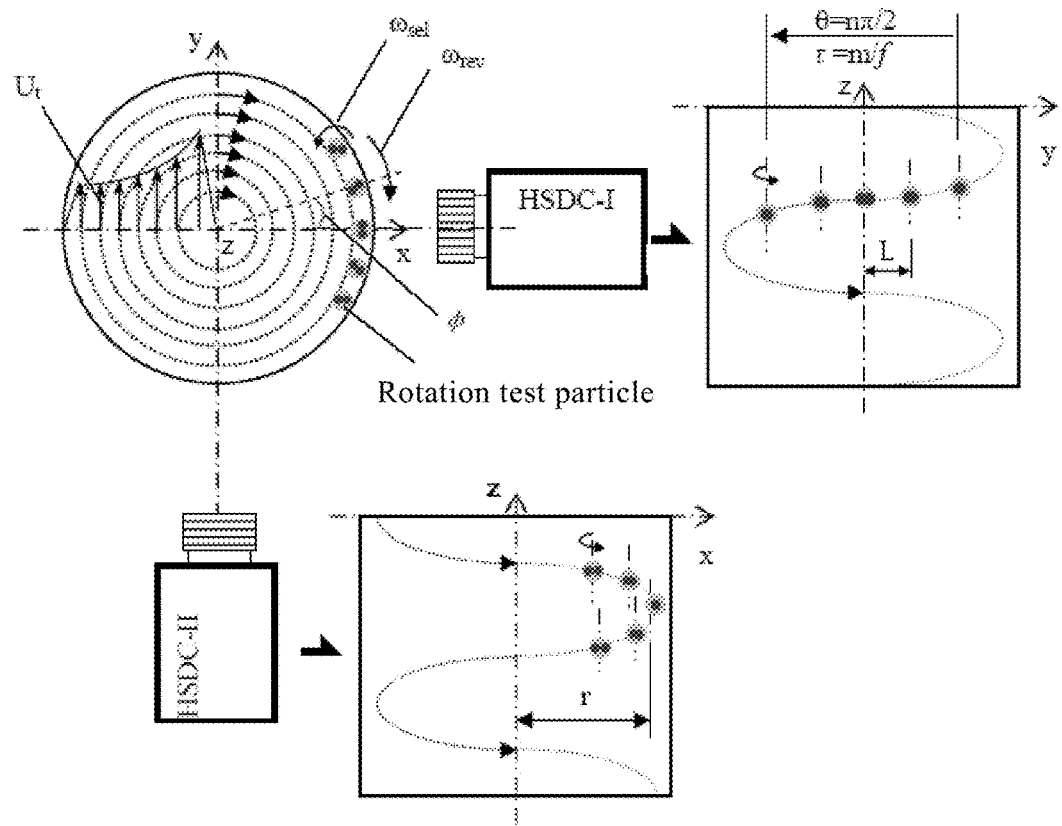
FIG. 2 is a schematic view showing the principle for testing the rotation of a microparticle in a liquid cyclone field using two orthogonally arranged high-speed digital cameras according to one or more embodiments shown and described herein.

FIG. 2 is a schematic view showing the principle for testing the rotation of a microparticle in a liquid microcyclone using two high-speed digital cameras according to at least one embodiment. The rotation motion of the microparticle in the cyclone field is mainly affected by the tangent velocity $U_t$ of the flow field. Based on the relationship between the distribution feature of the tangent velocity and the position of the particle in the cyclone field, it may be determined that the rotation of the particle and the whirling of the fluid are opposite in direction.

The rotation velocity of the particle $\omega_{sel}$ may be calculated as follows:

$$\omega_{sel} = \frac{\theta}{\tau} \quad (1)$$

$$\theta = \frac{n\pi}{2} \quad (2)$$

$$\tau = \frac{m}{f} \quad (3)$$

wherein $\theta$ is the rotational angle of the microparticle, n is the number of times the two inner cores in the particle overlap and separate in a group of image series taken by the high-speed digital camera (HSDC-I), $\tau$ is the time for recording the rotation of the particle, m is the number of the photographs recording the rotation motion of the particle, and f is the frame frequency of the high-speed digital camera.

The particle coordinates y and z may be determined according to the photographs taken by one of the high-speed digital cameras (HSDC-I); and the particle coordinates x and z may be determined according to the photographs taken by the other of the high-speed digital cameras (HSDC-II), wherein the maximum x value is defined as the instantaneous revolution radius r of the particle rotating in the zone to be tested. As such, an approximate motion trajectory of the particle in the zone to be tested may be determined thereby.

The method for calculating the revolution velocity of the particle is as follows:

$$\omega_{rev} = \frac{\alpha f}{2\pi} \times 60 \quad (4)$$

wherein $$\alpha = \sin^{-1}\frac{L}{r}.$$

L is the distance of the particle to the center of the cyclone field in the two dimensional image.

Figure 3:
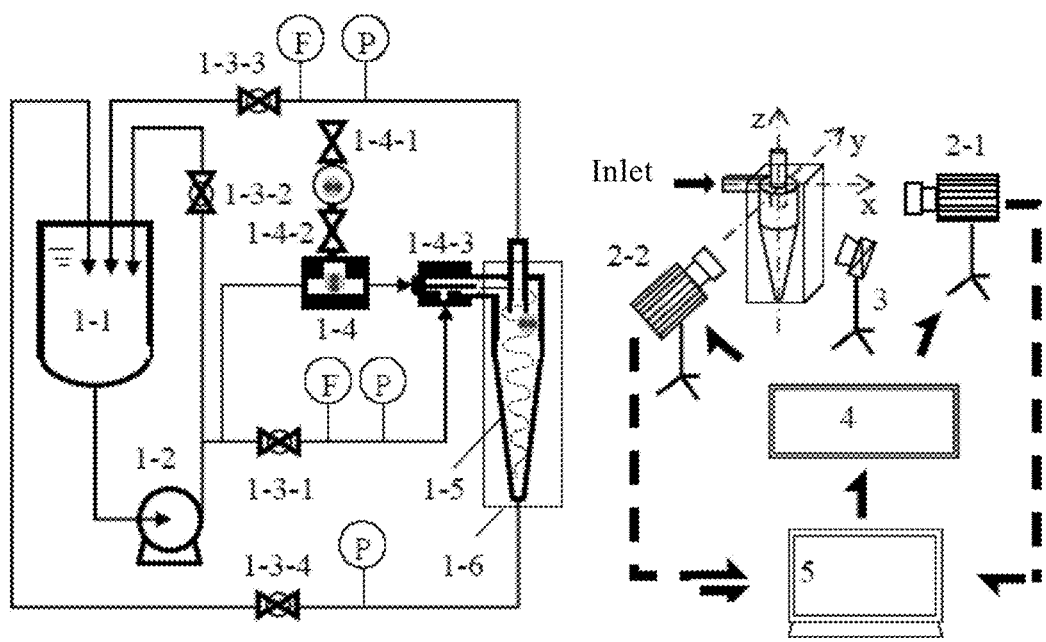
FIG. 3 is a schematic view showing a device for testing the rotation of a microparticle in a liquid-solid microcyclone using two orthogonally arranged high-speed digital cameras according to one or more embodiments shown and described herein.

FIG. 3 is a schematic view showing a device for testing the rotation of a microparticle in a liquid-solid microcyclone using two orthogonally arranged high-speed digital cameras according to at least one embodiment. This device includes a cyclone separation experimental apparatus 1, high-speed digital cameras 2, a large power LED light source 3, a trigger synchronizer 4 for the high-speed cameras, and a control computer 5.

The cyclone separation experimental apparatus comprises a liquid reservoir 1-1, wherein the liquid in the reservoir is pressurized by a pump 1-2. A control valve 1-3-1 and a backflow valve 1-3-2 are used to control the fluid flow into the optical quartz glass microcyclone 1-5 and the variation of the inlet pressure. A particle is added into a particle feeder 1-4 with the aid of the switch of valves 1-4-1 and 1-4-2. Due to the action of the pressure difference, the test particle is delivered to a particle feeding connector 1-4-3 at the entrance to the microcyclone. Test particles are injected continuously and uniformly into the inlet of the microcyclone through a pinhole which has an inner diameter of 1.5 mm and is located inside the particle feeding connector 1-4-3. A rectangular water jacket 1-6 made of clear glass is disposed around the microcyclone, wherein the water jacket is filled with the same medium as that in the reservoir 1-1, so as to reduce the test error caused by the light refraction on the curved surface of the microcyclone. Flow and pressure meters are arranged at the inlet of the microcyclone and the overflow outlet. A pressure meter is arranged at the underflow outlet. Flow control valves 1-3-3 and 1-3-4 are also arranged at the overflow outlet and the underflow outlet, respectively.

Figure 4:
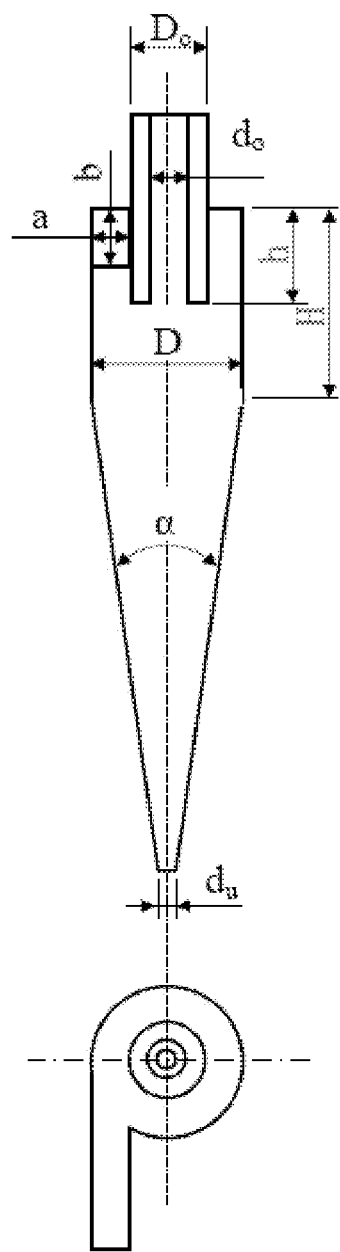
FIG. 4 is a schematic view showing the structure of an optical quartz glass microcyclone for providing a liquid cyclone field according to one or more embodiments shown and described herein.

FIG. 4 is a schematic view showing the structure of an optical quartz glass microcyclone for providing a liquid cyclone field according to at least one embodiment. a and b are the length and the height of the inlet, respectively, D is the inner diameter of the column section of the microcyclone (nominal diameter), $D_o$ is the outer diameter of the overflow pipe, $d_o$ is the inner diameter of the overflow pipe, h is the depth to which the overflow pipe is inserted, H is the height of the column section, $d_u$ is the inner diameter of the underflow outlet, and α is the taper angle.

The main advantages of the methods and devices described herein include: owing to the use of a transparent or translucent particle containing two inner cores as a test particle, the identifiability of the rotation motion of the particle in a cyclone field is increased greatly, and synchronous determination of the rotation of a microparticle in a low-viscosity strong cyclone field and its revolution around the geometric center of the cyclone field is realized.

EXAMPLES

The embodiments described herein will be further illustrated with reference to the following specific Examples. It is nevertheless to be appreciated that these Examples are only intended to exemplify the embodiments described herein without limiting their scope. The test methods in the following examples for which no specific conditions are indicated will be carried out generally under conventional conditions or under those conditions suggested by the manufacturers. Unless otherwise specified, all parts are parts by weight, and all percentages are percentages by weight.

Example 1

With the use of a test device as shown in FIG. 3, the rotation velocity of microparticles in an optical quartz glass microcyclone having a nominal diameter of 25 mm may be determined. The liquid medium was tap water at ambient temperature. The particle used was a translucent spherical polymer particle containing two inner cores having the same diameter and arranged centrosymmetrically, synthesized by microfluidic granulation technique. The average particle diameter is 450 microns, and the coefficient of variation (CV value) is 3%. It is generally accepted that a CV value of less than 5% indicates good monodispersity. The relative density of the particle is 1.15. Table 1 shows the revolution and rotation velocities of the microparticles in the column section of the optical quartz glass microcyclone having a nominal diameter of 25 mm, measured under different operating pressures of the device according to an embodiment of the method described herein. Table 2 shows the three dimensional trajectory coordinates of the microparticles in the cyclone field, reconstructed according to an embodiment of the method described herein when the operating pressure was 0.1 MPa.

TABLE 1

Revolution and rotation velocities of microparticles under different operating pressures

| | Operating pressure, MPa | | | | |
|---|---|---|---|---|---|
| | 0.10 | 0.14 | 0.18 | 0.22 | 0.26 |
| Revolution radius r, mm | 11.558 | 11.738 | 11.648 | 10.295 | 11.738 |
| Revolution velocity, r/min | 2336 | 2543 | 3032 | 4733 | 4202 |
| Rotation velocity, r/min | 24330 | 12697 | 9668 | 5427 | 11038 |

TABLE 2

Reconstructed three dimensional trajectory coordinates of microparticles in cyclone field

| x | y | z |
|---|---|---|
| 10.619 | 4.563 | 21.780 |
| 10.976 | 3.621 | 21.983 |
| 11.194 | 2.879 | 22.081 |
| 11.395 | 1.934 | 22.286 |
| 11.510 | 1.052 | 22.485 |
| 11.558 | 0.101 | 22.587 |
| 11.491 | −1.243 | 22.688 |
| 11.408 | −1.856 | 22.783 |
| 11.197 | −2.866 | 22.984 |
| 10.942 | −3.722 | 23.088 |
| 10.604 | −4.598 | 23.189 |

All of the documents mentioned in the disclosure are incorporated herein by reference, as if each of them were incorporated herein individually by reference. It is to be further understood that various changes or modifications can be made by those skilled in the art after reading the above teachings, and these equivalent variations fall in the scope defined by the accompanying claims of the application as well.

What is claimed is:

1. A synchronous high-speed photographing method for microparticle rotation in a liquid cyclone field, comprising:
   (1) using a transparent microparticle comprising two inner cores having the same diameter and arranged centrosymmetrically as a rotation test particle;
   (2) acquiring synchronously two groups of two dimensional image series of microparticle motion in the liquid cyclone field using two orthogonally arranged high-speed digital cameras; and
   (3) reconstructing a three dimensional motion trajectory of the transparent microparticle from the two groups of two dimensional image series, and determining a rotation velocity of the transparent microparticle in the liquid cyclone field at the same time.

2. The method of claim 1, wherein the rotation test particle is a spherical particle having a transparent or translucent shell and containing two centrosymmetrically arranged inner core particles which have a deep color and the same diameter, wherein the test particle has a diameter of less than 500 microns and high monodispersity (coefficient of variation <5%).

3. The method of claim 1, wherein the two high-speed digital cameras are arranged orthogonally, a synchronous photographing error is less than 10 microseconds, and a depth of field of the two high-speed cameras is no less than 20% of the diameter of the liquid cyclone field.

4. The method of claim 1, wherein the method reconstructs the three dimensional motion trajectory in a zone to be tested by fitting two dimensional motion trajectories of the transparent microparticle in the two groups of two dimensional image series.

5. The method of claim 1, wherein the method determines the rotation velocity of the transparent microparticle by analyzing the overlapping and separating frequency of projections of the two inner cores in the transparent microparticle in the two groups of two dimensional image series, wherein the test particle has a discrimination precision of rotational angle of 90 degrees.

6. The method of claim 1, wherein the method determines simultaneously a revolution motion of the transparent microparticle in the liquid cyclone field around a geometric center of the liquid cyclone field and a rotation motion around its own instantaneous axis.

7. The method of claim 1, wherein the liquid cyclone field has a maximum tangent velocity of no more than 10 m/s.

8. The method of claim 5, wherein the method uses only one of the high-speed cameras to determine the rotation velocity of the transparent microparticle, and uses the other one for three dimensional positioning.

9. A synchronous high-speed photographing device for microparticle rotation in a liquid cyclone field, comprising:
   a cyclone separation experimental apparatus for providing a cyclone field to be tested; two high-speed digital cameras for synchronous measurement; a large power LED cold light source for providing strong white light; a synchronous trigger for the high-speed digital cameras; and a computer for controlling the high-speed digital cameras and storing data.

10. The device of claim 9, wherein the cyclone separation experimental apparatus is a circulating system, wherein the experimental apparatus comprises a reservoir for storing liquid and a vortex pump connected to the reservoir for pressurizing the liquid, wherein an outlet of the vortex pump divides into two routes, along one of which a fluid goes back to the reservoir through a backflow valve, along the other of which another liquid goes through a flow valve and a particle feeding connector and then enters an optical quartz glass microcyclone, wherein the fluid from both the top and the bottom of the quartz glass microcyclone returns to the reservoir, wherein a pressure meter is arranged at each of an inlet and two outlets of the quartz glass microcyclone, and a flow meter and a control valve are further arranged at the inlet and a top outlet.

11. The device of claim 9 or 10, wherein a stainless steel needle having an inner diameter of 1.5 mm is disposed inside an particle feeding connector, wherein a needle injects the microparticle through an inlet of a quartz glass microcyclone into the cyclone field.

12. The device of claim 9, wherein one of the high-speed digital cameras has a frame frequency of 10000 fps or more, a minimum exposure time of 1 microsecond or less, and a resolution of 800×600 or more; and the other of the high-speed digital cameras has a frame frequency of 2000 fps or more, a minimum exposure time of 1 microsecond or less, and a resolution of 800×600 or more.

13. The device of claim 9, wherein the two high-speed digital cameras use macrolens.

14. The device of claim 9, wherein the large power LED cold light source has a lighting color temperature of 5500-8000K and a luminous flux of 12000 Lm or more.

15. The device of claim 10, wherein the optical quartz glass microcyclone has a nominal diameter of 40 mm or less, an inlet operating pressure of 0.1 MPa-0.3 MPa, and an operating temperature of 50° C. or less.

16. The device of claim 12, wherein the high-speed digital camera can photograph the microparticle rotation alone.

* * * * *